US005667778A

United States Patent [19]

Atala

[11] Patent Number: 5,667,778
[45] Date of Patent: Sep. 16, 1997

[54] INJECTABLE BLADDER MUSCLE CELLS-POLYMER SUSPENSION FOR TREATMENT OF VESICOURETERAL REFLUX AND INCONTINENCE

[75] Inventor: Anthony Atala, Newton, Mass.

[73] Assignee: Children's Medical Center Corporation, Boston, Mass.

[21] Appl. No.: 228,678

[22] Filed: Apr. 18, 1994

Related U.S. Application Data

[63] Continuation-in-part of Ser. No. 56,140, Apr. 30, 1993.
[51] Int. Cl.$^6$ ............................................. A61K 35/34
[52] U.S. Cl. .......................... 424/93.7; 623/11; 623/14; 424/423
[58] Field of Search ........................ 424/93.7, 423; 623/14, 11

[56] References Cited

U.S. PATENT DOCUMENTS

| | | | |
|---|---|---|---|
| 4,673,566 | 6/1987 | Goosen et al. | 424/93.7 |
| 5,041,138 | 8/1991 | Vacanti et al. | 623/16 |
| 5,053,050 | 10/1991 | Itay | 623/16 |
| 5,294,446 | 3/1994 | Schlameus et al. | 424/93.7 |
| 5,336,263 | 8/1994 | Ersek et al. | 623/11 |

FOREIGN PATENT DOCUMENTS

| | | |
|---|---|---|
| 9407999 | 4/1994 | WIPO. |
| WO 94/21299 | 9/1994 | WIPO. |

OTHER PUBLICATIONS

Yarom et al., Virchows Arch B Cell Pathol. Incl. Mol. Pathol. 41(1–2):171–180 (1982).

Jones, Exp. Neurol. 66(3):602–610 (1979).

Atala, Anthony, et al., "Laparoscopic correction of vesicoureteral reflux" *J. Urol.* 150:748 (1993).

Atala, Anthony, et al., "Endoscopic Treatment of Reflux with Autologous Bladder Muscle Cells," American Academy of Pediatrics meeting held in Dallas, Texas on Oct. 23, 1994, Abstract.

Atala, Anthony, et al., "Injectable Alginate Seeded with Chondrocytes as a Potential Treatment for Vesicoureteral Reflux," Annual Meeting of the Section on Urology, American Academy of Pediatrics, Oct. 10–15, 1992, subsequently published in the *Journal of Urology*, 150:745–7477 (Aug. 1993), Abstract.

Atala, Anthony and Anthony J. Casale, "Management of Primary Vesicoureteral Reflux," *Infections in Urology* 39–43 (Mar./Apr. 1990).

Atala, Anthony, et al., "Endoscopic treatment of vesicoureteral reflux with a self-detachable balloon system" *J. Urol.* 148:724 (1992).

Buckley, J. F., et al., "Endoscopic correction of vesicoureteric reflux with injectable silicone microparticles" *J. Urol.* 149 Abstract 259A (1993).

Claes, H., et al., "Pulmonary migration following periurethal polyetrafluoroethylene injection for urinary incontinence" *J. Urol.*, 142:821 (1989).

Henly, David R., et al., "Particulate silicone for use in periurethral injections: a study of local tissue effects and a search for migration" *J. Urol.* 147 Abstract 376A (1992).

Leonard, Michael P., et al. "Endoscopic injection of glutaraldehyde cross–linked bovine dermal collagen for correction of vesicoureteral reflux" *J. Urol.* 145:115 (1991).

Malizia, Anthony A., et al. "Migration and granulomatous reaction after periurethral injection of polymer (polytetrafluoroethylene)" *JAMA*, 251:3277 (1984).

Matouschek, E.: Die Behandlung des vesikorenalen Refluxes durch transueterale Einspritzung von polytetrafluoroethylenepast. *Urologe*, 20:263 (1981).

Paige, Keith T., et al., "De Novo Cartilage Generation Utilizing Calcium Alginate–Chondrocyte Constructs," 1993 Plastic Surgery Research Council meeting held in Houston, Texas between Apr. 28, 1993, and May 1, 1993, Abstract.

Contemporary Urology (Mar. 1993).

Atala et al. "Injectable Aliginate Seeded With Human Bladder Muscle Cells As A Potential Treatment For Vesicoueteral Reflux", American Urological Association, Eighty–Ninth Annual Meeting, May 14–19, 1994, and Journal of Urology 151:362 A (May 1994).

*Primary Examiner*—Jean C. Witz
*Attorney, Agent, or Firm*—Arnall Golden & Gregory

[57] ABSTRACT

A method of treatment of vesicoureteral reflux, incontinence and other defects is described wherein bladder muscle cells are mixed with a liquid polymeric material to form a suspension. This is injected into the area of the defect, in an amount effective to yield a muscle area that provides the required control over the passage of urine or otherwise corrects the defect.

19 Claims, 1 Drawing Sheet

INJECTABLE BLADDER MUSCLE CELLS-POLYMER SUSPENSION FOR TREATMENT OF VESICOURETERAL REFLUX AND INCONTINENCE

This is a continuation-in-part of U.S. Ser. No. 08/056,140 filed Apr. 30, 1993 by Keith T. Paige, Linda G. Cima, Charles A. Vacanti and Anthony Atala entitled "Injectable Polysaccharide-Cell Compositions".

BACKGROUND OF THE INVENTION

The present invention is generally in the area of medical treatments, and specifically relates to a method for correcting vesicoureteral reflux, incontinence and other defects.

Vesicoureteral reflux.

Vesicoureteral reflux is a condition wherein there is an abnormal development of the ureteral bud as it enters the bladder during embryologic development. The shortened course of the ureter through the bladder musculature decreases the ureteral resistance and allows for urine to reflux from the bladder reservoir back up into the ureter and into the kidney. With this condition, bacteria which may occasionally be present in the bladder through retrograde urethral transport, can reach the kidneys and cause recurrent pyelonephritis. In addition, the constant back pressure of the urine into the calyces and renal pyramids results in mechanical damage to the renal parenchyma. If untreated, urinary vesicoureteral reflux can cause loss of renal parenchyma, and in some instances, renal failure, as reviewed by Atala and Casale, *Infections in Urology* 39–43 (March/April 1990). In 1960, 70% of the patients with renal failure were described as having vesicoureteral reflux as the primary etiology. With the advent of new diagnostic and treatment modalities, patients with vesicoureteral reflux now account for less than 1% of the renal failure population.

In the past, vesicoureteral reflux was usually diagnosed with a voiding cystogram after the child presented with repeated episodes of pyelonephritis. With the increased use of prenatal and postnatal sonography, hydronephrosis is more detectable, prompting further radiologic workup and earlier detection, as reported by Atala and Casale. Vesicoureteral reflux is graded depending on the severity. Grade 1 reflux signifies that urine is seen refluxing from the bladder up to the ureter only; in grade 2 reflux, urine refluxes into the ureter and calyceal dilatation. Grade 4 and 5 reflux are more severe, showing ureteral tortuosity and further calyceal blunting and dilatation, respectively.

The treatment of vesicioureteral reflux has been well established over the last decade. Initially it was believed that all patients with reflux would require surgery. Another school of management soon proposed that only medical therapy with antibiotics was required. It is now well established that the treatment of reflux depends on many factors, including the severity of reflux, associated congenital abnormalities, and the social situation of the child (parental compliance with medical treatment). Medical treatment is usually recommended for patients with grade 1 and 2 reflux, which usually resolve on their own as the bladder/ureteral configuration changes with growth. Grade 3 reflux is generally managed with medical therapy unless it persists or breakthrough infections occur while on antibiotic suppression. Surgical treatment is usually required for grade 4 and 5 reflux.

Medical treatment implies that the patient is treated with daily suppressive antibiotics. A close follow-up is required in these patients, generally consisting of a catheterized urine culture every three months, an ultrasound exam and serum analysis every six months, a fluoroscopic or nuclear voiding cystourethrogram every year, and a DMSA renal scan every two years. Surgical treatment consists of an open surgery wherein a low abdominal incision is made, the bladder is entered, the ureters are mobilized and new ureteral submucosal tunnels are created; thereby extending the muscular backing of the ureter which increases their resistance. These patients require a general endotracheal anesthetic for a four to five hour surgery, an epidural catheter for both intraoperative and postoperative pain control, a bladder catheter for drainage, a perivesical drain, and a five to six day hospital stay. Antibiotic therapy and bladder antispasmodics are required post-operatively.

Although open surgical procedures for the correction of reflux have excellent results in the hands of experienced surgeons, it is associated with a well recognized morbidity, including pain and immobilization of a lower abdominal incision, bladder spasms, hematuria, and post-operative voiding frequency in some children. In an effort to avoid open surgical intervention, widespread interest was initiated by Matouschek's clinical experience with the endoscopic injection of Teflon™ (polytetrafluoroethylene) paste subureterally in 1984, as reported in Matouschek, E.: Die Behandlung des vesikorenalen Refluxes durch transueterale Einspritzung von polytetrafluoroethylenepast. *Urologe*, 20:263 (1981). With this technique, a cystoscope is inserted into the bladders, a needle is inserted through the cystoscope and placed under direct vision underneath the refluxing ureter in the submucosal space, and Teflon™ paste is injected until the gaping ureteric orifice configuration changes into a half-moon slit. The Teflon™ paste, injected endoscopically, corrects the reflux by acting as a bulking material which increases ureteral resistance. However, soon after the introduction of this treatment, a controversy regarding the use of Teflon™ paste ensued. Malizia et al. "Migration and granulomatous reaction after periurethral injection of polymer (polytetrafluoroethylene)" *JAMA*, 251:3277 (1984), showed granuloma formation and particulate migration to the brain, lungs, and lymph nodes in animal studies. Polytetrafluoroethylene migration and granuloma formation have also been reported in humans by Claes et al., "Pulmonary migration following periurethral polyetrafluoroethylene injection for urinary incontinence" *J. Urol.,* 142:821 (1989). The safety of Teflon™ for human use was questioned, and the paste was thereafter banned by the FDA.

However, there are definite advantages in treating vesicoureteral reflux endoscopically. The method is simple and can be completed in less than fifteen minutes, it has a success rate of greater than 85% with low morbidity and it can be performed in an outpatient basis, as reported by Atala et al, "Endoscopic treatment of vesicoureteral reflux with a self-detachable balloon system" *J. Urol.* 148:724 (1992). The goal of several investigators has been to find alternate implant materials which would be safe for human use.

Bovine dermal collagen preparations have been used to treat reflux endoscopically. However, only 58.5% of the patients were cured at one year follow-up, as described by Leonard et al, "Endoscopic injection of glutaraldehyde cross-linked bovine dermal collagen for correction of vesicoureteral reflux" *J. Urol.* 145:115 (1991). The collagen implant volume decreases with time, which results in high percentage of recurrence of reflux, over 90% within 3 years. The high failure rate with this substance presents a high risk to the unaware patient of developing renal damage after treatment.

A paste consisting of textured microparticles of silicone, suspended in a hydrogel, has been injected subureterally to correct reflux with an initial success rate of 91% in one European study, as reported by Buckley et al., "Endoscopic correction of vesicoureteric reflux with injectable silicone microparticles" *J. Urol.* 149:259A (1993). However, distant particle migration has been observed in animal models, as reported by Henly et al., "Particulate silicone for use in periurethral injections: a study of local tissue effects and a search for migration" *J. Urol.* 147:376A (1992). Approximately thirty percent of the silicone particles have a diameter which is less than 100 μm. This suggests that thirty percent of the silicone particles have a potential for distant organ migration through the macrophage system. The manufacturer of this technology tried unsuccessfully to obtain FDA approval, and subsequently filed for bankruptcy.

Laparoscopic correction of reflux has been attempted in both an animal model (Atala et al, "Laparoscopic correction of vesicoureteral reflux" *J. Urol.* 150:748 (1993)) and humans (Atala, "Laparoscopic treatment of vesicoureteral reflux"*Dial Ped Urol* 14:212 (1993)) and is technically feasible. However, at least two surgeons with laparoscopic expertise are needed, the length of the procedure is much longer than with open surgery, the surgery is converted from an extraperitoneal to an intraperitoneal approach, and the cost is higher due to both increased operative time and the expense of the disposable laparoscopic equipment.

Despite the fact that over a decade has transpired since the Teflon™ controversy, little progress has been made in this area of research. The ideal substance for the endoscopic treatment of reflux should be injectable, non-antigenic, non-migratory, volume stable, and safe for human use (Atala et al, 1992).

Urinary incontinence.

Urinary Incontinence is the most common and the most intractable of all GU maladies. Urinary incontinence, or the inability to retain urine and not void urine involuntarily, is dependent on the interaction of two sets of muscles. One is the detrusor muscle, a complex of longitudinal fibers forming the external muscular coating of the bladder. The detrusor is activated by parasympathetic nerves. The second muscle is the smooth/striated muscle of the bladder sphincter. The act of voiding requires the sphincter muscle be voluntarily relaxed at the same time that the detrusor muscle of the bladder contracts. As a person ages, his ability to voluntarily control the sphincter muscle is lost in the same way that general muscle tone deteriorates with age. This can also occur when a radical event such as paraplegia "disconnects" the parasympathetic nervous system causing a loss of sphincter control. In different patients, urinary incontinence exhibits different levels of severity and is classified accordingly.

The most common incontinence, particular in the elderly, is urge incontinence. This type of incontinence is characterized by an extremely brief warning following by immediate urination. This type of incontinence is caused by a hyperactive detrusor and is usually treated with "toilet training" or medication. Reflex incontinence, on the other hand, exhibits no warning and is usually the result of an impairment of the parasympathetic nerve system such as a spinal cord injury.

Stress incontinence is most common in elderly women but can be found in women of any age. It is also commonly seen in pregnant women. This type of incontinence accounts for over half of the total number of cases. It is also found in men but at a lower incidence. Stress incontinence is characterized by urine leaking under conditions of stress such as sneezing, laughing or physical effort. There are five recognized categories of severity of stress incontinence, designated as types as 0, 1, 2a, 2b, and 3. Type 3 is the most severe and requires a diagnosis of intrinsic Sphincter Deficiency or ISD (Contemporary Urology, March 1993). There are many popular treatments including weight loss, exercise, medication and in more extreme cases, surgical intervention. The two most common surgical procedures involve either elevating the bladder neck to counteract leakage or constructing a lining from the patient's own body tissue or a prosthetic material such as PTFE to put pressure on the urethra. Another option is to use prosthetic devices such as artificial sphincters to external devices such as intravaginal balloons or penile clamps. For treatment of type 3 stress incontinence, there has been a recent trend toward injection of Teflon™ or collagen paste around the sphincter muscle in order to "beef up" the area and improve muscle tone. None of the above methods of treatment, however, are very effective for periods in excess of a year.

Overflow incontinence is caused by anatomical obstructions in the bladder or underactive detrustors. It is characterized by a distended bladder which leads to frequent urine leakage. This type of incontinence is treated acutely by catheterization and long-term by drug therapy. Enuresis or bed-wetting is a problem in pediatrics and is controlled by various alarming devices and pads with sensors. Enuresis is not considered a serious problem unless it lasts beyond the age of four or five. Finally, there is true functional incontinence which occurs in patients with chronic impairment either of mobility or mental function. Such patients are usually treated by the use of diapers, incontinence pads or continuous catheterization (BBI, 1985 Report 7062).

It is therefore an object of the present invention to provide a method and material for treating vesicoureteral reflux, incontinence, and other defects which results in a natural and permanent cure to the defect.

It is a further object of the present invention to provide a method and material for treating vesicoureteral reflux, incontinence, and other defects which is quick, simple, safe, and relatively non-invasive.

SUMMARY OF THE INVENTION

A method of treatment of vesicoureteral reflux, incontinence and other defects is described wherein bladder muscle cells are mixed with a liquid polymeric material, such as alginate which can be solidified in vivo, to form a cell suspension, which is injected into the area of the defect, in an amount effective to yield a muscle area that corrects the defect, for example, which provides the required control over the passage of urine.

As described in the examples, human bladder muscle specimens are obtained and processed within one hour after surgical removal. In the preferred embodiment, muscle cells are mixed with a biodegradable liquid polymer such as alginate, a biodegradable copolymer of gluronic and mannuronic acid, which is designed to solidify at a controlled rate when contacted with calcium salts. The cells are then injected at the desired site where they proliferate and correct the defect. Examples demonstrate efficacy in mice.

DETAILED DESCRIPTION OF THE INVENTION

Figure 1:
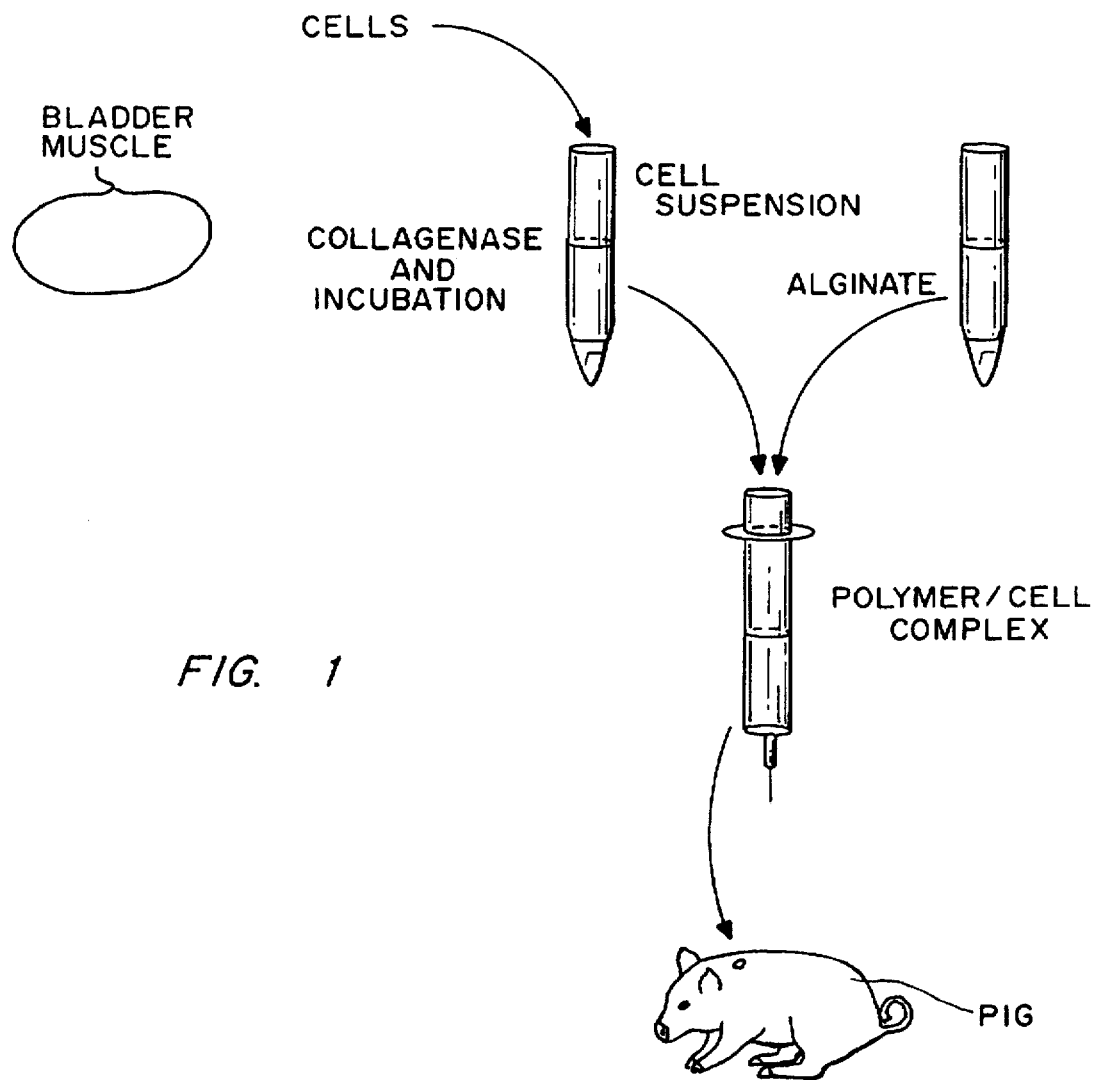
FIG. 1 is a schematic of injection of a polymer-muscle cell suspension into a region for control of vesicoureteral reflux.

A biodegradable polymer, embedded with muscle cells, serves as a synthetic substrate for the injectable delivery and maintenance of muscle architecture in humans that satisfies all the requirements for an ideal injectable substance. A biopsy of the bladder can be easily and quickly performed cystoscopically followed by muscle cell processing and endoscopic injection of the autologous muscle cell/polymer suspension for the treatment reflux, incontinence and other defects.

Studies show that muscle cells can be easily harvested and combined with alginate in vitro, the suspension can be easily injected cystoscopically and the muscle tissue formed is able to correct vesicoureteral reflux without any evidence of obstruction. The ideal injectable substance for the endoscopic treatment of reflux should be a natural bulking agent which is non-antigenic, non-migratory, and volume stable. Autologous muscle cells seem to fulfill all of these requirements. Since the muscle cells are autologous, this method of treatment does not require FDA approval. The procedure can be performed under 15 minutes, with a short period of a mask anesthetic, in the outpatient unit, without any need for a hospital stay. Neither vesical nor perivesical drainage is required. Since the whole procedure is done endoscopically and the bladder is not entered surgically, there is no postoperative discomfort whatsoever. The patient can return to a normal level of activity almost immediately.

Source of Cells

In the preferred embodiment, cells of the same species and preferably immunological profile are obtained by biopsy, either from the patient or a close relative, which are then grown to confluence in culture using standard conditions as described below in Example 1 and used as needed. If cells that are likely to elicit an immune reaction are used, such as human muscle cells from immunologically distinct individual, then the recipient can be immunosuppressed as needed, for example, using a schedule of steroids and other immunosuppressant drugs such as cyclosporine. However, in the most preferred embodiment, the cells are autologous.

Cells obtained by biopsy are harvested and cultured, passaging as necessary to remove contaminating non-bladder muscle cells.

Polymer Solutions

In the preferred embodiment described herein, calcium alginate and certain other polymers that can form ionic hydrogels which are malleable are used to encapsulate cells. The hydrogel is produced by cross-linking the anionic salt of alginic acid, a carbohydrate polymer isolated from seaweed, with calcium cations, whose strength increases with either increasing concentrations of calcium ions or alginate. The alginate solution is mixed with the cells to be implanted to form an alginate suspension. Then the suspension is injected directly into a patient prior to hardening of the suspension. The suspension then hardens over a short period of time due to the presence in vivo of physiological concentrations of calcium ions.

The polymeric material which is mixed with cells for implantation into the body should form a hydrogel. A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides such as alginate, polyphosphazines, and polyacrylates, which are crosslinked ionically, or block copolymers such as Pluronics™ or Tetronics™, polyethylene oxide-polypropylene glycol block copolymers which are crosslinked by temperature or pH, respectively. Other materials include proteins such as fibrin, polymers such as polyvinylpyrrolidone, hyaluronic acid and collagen.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. Due to these mild conditions, alginate has been the most commonly used polymer for hybridoma cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

Polyphosphazenes are polymers with backbones consisting of nitrogen and phosphorous separated by alternating single and double bonds. Each phosphorous atom is covalently bonded to two side chains ("R"). The repeat unit in polyphosphazenes has the general structure (1):

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. For example, a polyanionic poly[bis(carboxylatophenoxy)] phosphazene (PCPP) can be synthesized, which is crosslinked with dissolved multivalent cations in aqueous media at room temperature or below to form hydrogel matrices.

Bioerodible polyphosphazines have at least two differing types of side chains, acidic side groups capable of forming salt bridges with multivalent cations, and side groups that hydrolyze under in vivo conditions, e.g., imidazole groups, amino acid esters, glycerol and glucosyl. The term bioerodible or biodegrable, as used herein, means a polymer that dissolves or degrades within a period that is acceptable in the desired application (usually in vivo therapy), less than about five years and most preferably less than about one year, once exposed to a physiological solution of pH 6–8 having a temperature of between about 25° C. and 38° C. Hydrolysis of the side chain results in erosion of the polymer. Examples of hydrolyzing side chains are unsubstituted and substituted imidizoles and amino acid esters in which the group is bonded to the phosphorous atom through an amino linkage (polyphosphazene polymers in which both R groups are attached in this manner are known as polyaminophosphazenes). For polyimidazolephosphazenes, some of the "R" groups on the polyphosphazene backbone are imidazole rings, attached to phosphorous in the backbone through a ring nitrogen atom. Other "R" groups can be organic residues that do not participate in hydrolysis, such as methyl phenoxy groups or other groups shown in the scientific paper of Allcock, et al., *Macromolecule* 10:824–830 (1977).

Methods for synthesis and the analysis of various types of polyphosphazenes are described by Allcock, H. R.; et al., *Inorg. Chem.* 11, 2584 (1972); Allcock, et al., *Macromolecules* 16, 715 (1983); Allcock, et al., *Macromolecules* 19, 1508 (1986); Allcock, et al., *Biomaterials*, 19, 500 (1988); Allcock, et al., *Macromolecules* 21, 1980 (1988); Allcock, et al., *Inorg. Chem.* 21(2), 515–521 (1982); Allcock, et al., *Macromolecules* 22, 75 (1989); U.S. Pat. Nos. 4,440,921, 4,495,174 and 4,880,622 to Allcock, et al.; U.S. Pat. No. 4,946,938 to Magill, et al.; and Grolleman, et al., *J. Controlled Release* 3, 143 (1986), the teachings of which are specifically incorporated herein by reference.

Methods for the synthesis of the other polymers described above are known to those skilled in the art. See, for example *Concise Encyclopedia of Polymer Science* and *Polymeric Amines and Ammonium salts*, E. Goethals, editor (Pergamen Press, Elmsford, N.Y. 1980). Many polymers, such as poly (acrylic acid), are commercially available.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts, e.g., $R_3N^+$—WV—$^+NR_3$ can also be used. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005M have been demonstrated to cross-link the polymer. Higher concentrations are limited by the solubility of the salt.

The preferred anions for cross-linking of the polymers to form a hydrogel are divalent and trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a semipermeable surface membrane. Examples of materials that can be used include polymers having basic reactive groups such as amine or imine groups, having a preferred molecular weight between 3,000 and 100,000, such as polyethylenimine and polylysine. These are commercially available. One polycation is poly(L-lysine); examples of synthetic polyamines are: polyethyleneimine, poly(vinylamine), and poly(allyl amine). There are also natural polycations such as the polysaccharide, chitosan.

Polyanions that can be used to form a semi-permeable membrane by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

Cell Suspensions

Preferably the polymer is dissolved in an aqueous solution, preferably a 0.1M potassium phosphate solution, at physiological pH, to a concentration forming a polymeric hydrogel, for example, for alginate, of between 0.5 to 2% by weight, preferably 1%, alginate. The isolated bladder muscle cells are suspended in the polymer solution to a concentration of between 1 and 50 million cells/ml, most preferably between 10 and 20 million cells/ml.

Injection of Cells

Vesicoureteral reflux is one of the most common congenital defects in children, affecting approximately 1% of the population. Although all patients do not require surgical treatment, it is still one of the most common procedure performed in children. Over 600 ureteral reimplants are performed yearly at Children's Hospital in Boston, Mass. This translates to an approximately saving of 3600 inpatient hospital days per year at this institution alone, if the endoscopic treatment described herein is used instead of open surgery.

In addition to its use for the endoscopic treatment of reflux, the system of injectable autologous muscle cell may also be applicable for the treatment of other medical conditions, such as urinary and rectal incontinence, dysphonia, plastic reconstruction, and wherever an injectable permanent biocompatible material is needed.

As described herein, an injectable biodegradable polymer as a delivery vehicle for muscle cells is useful in the treatment of reflux and incontinence. In the preferred embodiment, a bladder muscle biopsy is obtained under anesthesia from a patient with vesicoureteral reflux, the isolated muscle cells are mixed with alginate, and the muscle cell-alginate solution is injected endoscopically in the subureteral region to correct reflux, as shown in FIG. 1. The time to solidification of the alginate-cell solution may be manipulated by varying the concentration of calcium as well as the temperature at which the muscle cells are added to the alginate. The use of autologous bladder muscle cells cells precludes an immunologic reaction. Solidification of the alginate impedes its migration until after it is degraded. The suspension can be injected through a cystoscopic needle, having direct visual access with a cystoscope to the area of interest, such as for the treatment of vesicoureteral reflux or urinary incontinence. In addition to the use of the muscle cell-polymer suspension for the treatment of reflux and incontinence, the suspension can also be applied to reconstructive surgery, as well as its application anywhere in the human body where a biocompatible permanent injectable material is necessary. The suspension can be injected endoscopically, for example through a laryngoscope for injection into the vocal chords for the treatment of dysphonia, or through a hysteroscope for injection into the fallopian tubes as a method of rendering the patient infertile, or through a proctoscope, for injection of the substance in the perirectal sphincter area, thereby increasing the resistance in the sphincter area and rendering the patient continent of stool.

The suspension can be injected via a syringe and needle directly into a specific area wherever a bulking agent is desired, i.e., a soft tissue deformity such as that seen with areas of muscle atrophy due to congenital or acquired diseases or secondary to trauma, burns, and the like. An example of this would be the injection of the suspension in the upper torso of a patient with muscular atrophy secondary to nerve damage.

The suspension can also be injected as a bulking agent for hard tissue defects, such as bone or cartilage defects, either congenital or acquired disease states, or secondary to trauma, burns, or the like. An example of this would be an injection into the area surrounding the skull where a bony deformity exists secondary to trauma. The injunction in these instances can be made directly into the needed area with the use of a needle and syringe under local or general anesthesia.

The suspension could also be injected percutaneously by direct palpation, such as by placing a needle inside the vas deferens and occluding the same with the injected bulking substance, thus rendering the patient infertile. The suspension could also be injected through a catheter or needle with fluoroscopic, sonographic, computed tomography, magnetic resonance imaging or other type of radiologic guidance. This would allow for placement or injection of this substance either by vascular access or percutaneous access to specific organs or other tissue regions in the body, wherever a bulking agent would be required.

Further, this substance could be injected through a laparoscopic or thoracoscope to any intraperitoneal or extraperitoneal or thoracic organ. For example, the suspension could be injected in the region of the gastro-esophageal junction for the correcting of gastroesophageal reflux. This could be performed either with a thoracoscope injecting the substance in the esophageal portion of the gastroesophageal region, or via a laparoscope by injecting the substance in the gastric portion of the gastroesophageal region, or by a combined approach.

The present invention will be further understood by reference to the following non-limiting examples. The examples demonstrate that human bladder muscle cell-alginate suspensions are injectable, non-migratory, and appear to conserve their volume and that autologous bladder muscle cells are useful in the endoscopic treatment of vesicoureteral reflux.

EXAMPLE 1

Isolation and Characterization of Human Bladder Muscle Cells Expanded In Vitro.

Cell Culture:

Human Tissue Origin. Human bladder tissue specimens were obtained and processed within one hour after surgical removal at Children's Hospital, Boston. The specimens varied in size, ranging from one $cm^2$ to four $cm^2$. The specimens were transported to Hanks balanced salt solution containing 10 mM HEPES and 100 KIU apoprotein.

Smooth Muscle Cells. Muscle cells were obtained by mincing small detrusor muscle fragments to approximately 0.5 mm diameter and using these as explants in 100 mm tissue culture dishes containing 10 mL of DMEM supplemented with 10% fetal calf serum. Approximately 30 explants of similar size were added to each dish. Medium was changed twice a week. Outgrowth was routinely observed at 72 hr after explants were placed in culture. When cultures were 80% confluent, the cells were trypsinized and passaged. Cell populations highly enriched in elongated, striated cells were routinely obtained using this method. Cell strains were stained with a-actin antibody to verify their muscle phenotype.

Results. Populations of fusiform, striated cells could be obtained from the bladder biopsy specimens by dissection of the muscle layer followed by explant culture of the muscle fragments in DMEM supplemented with 10% calf-serum. Immunostaining with a monoclonal antibody which specifically recognized a-actin verified the muscle phenotype. These data indicate that highly proliferative populations of smooth muscle can be obtained from small biopsy specimens. The muscle cells can also be grown transiently in serum-free defined media which renders the cells free from any impurities.

EXAMPLE 2

Injection of cell suspensions into mice.

Using a 22 gauge needle, 20 nude mice were injected with a 500 microliter solution of muscle cells and alginate. Each mouse had two injection sites consisting of either control, or a solution of ten million human bladder cells per cc of alginate (32 injection sites). Injections of alginate alone or bladder muscle cells alone served as controls. Animals were sacrificed at two, four, six and eight weeks after implantation. Histologic examination of the injection areas demonstrated evidence of muscle formation in the muscle/alginate injection sites. Immunohistochemical analysis using an anti-desmin antibody indicated that the cells maintained a program of muscular differentiation. Examination of the injection sites with increasing periods of time, showed that the alginate was progressively replaced by muscle. The size of the muscle-alginate complex appeared to be uniform and stable. In both control groups (alginate alone or muscle cells alone) there were no muscle cells evident. Histologic analysis of distant organs showed no evidence of bladder muscle cells or alginate migration or granuloma formation.

EXAMPLE 3

Correction of vesicouretral reflux in pigs using bladder muscle cells implanted in an alginate gel.

Materials and Methods

Animal model of vesicoureteral reflux. The pig was used for this study because of the similarities between porcine and human bladders and kidneys. The Hanford mini-pig was used for the convenience of its smaller size. Bilateral vesicoureteral reflux was created in four mini-swine using the open bladder technique, which consists of unroofing the entire intravesical ureter, as described by Vacanti, et al., "Synthetic polymers seeded with chondrocytes provide a template for new cartilage formation" *Plastic and Recon. Surg.* 88:753 (1991).

Three months after the procedure, the presence of bilateral reflux was assessed by conventional radiographic cystography using an iodinated contrast agent, and by sonography using sonicated albumin, as described by Vacanti, et al., "Tissue engineered growth of new cartilage in the shape of a human ear using synthetic polymers seeded with chondrocytes" *Mat. Res. Soc. Proc.* 252:367 (1992). Excretory urography was performed to detect any evidence of obstruction.

Cell Harvest. A segment of bladder muscle was obtained from each animal. Muscle cells were harvested and plated separately in vitro. After expansion, the cells were individually quantitated and concentrated to $20 \times 10^6$ cells per cc.

Autologous bladder muscle cell-calcium alginate suspension. Two percent weight/volume sodium alginate (0.1M $K_2PO_4$, 0.135M NaCl, pH 7.4, Protan, Portsmouth, N.H.) was made and sterilized in ethylene oxide. A 1.5 ml aliquot of $20 \times 10^6$ cells/ml bladder muscle cell suspension was added to an equal volume of sodium alginate solution for a final alginate concentration of 1%. The bladder muscle cell-sodium alginate suspension was kept at 32° C. Immediately prior to injection, calcium sulfate (0.2 g/ml) was added to the bladder muscle cell-sodium alginate suspension. The mixture was vortexed and stored in ice until injection. The gelling process was initiated with the addition of calcium sulfate, which allowed the suspension to remain in a liquid state for approximately 40 minutes.

Experimental study. Mini-pigs were anesthetized with intramuscular injections of 25 ml/kg ketamine and 1 ml/kg acylpromazine. Additional anesthesia was obtained with an intramuscular administration of 25 mg/kg ketamine and 10 mg/kg of xylazine. Animals were placed in a supine position. With a 15.5 French cystoscope introduced into the bladder, a 21 gauge needle was inserted in the subureteral region of the right refluxing ureter. Approximately 2 to 3 ml of the autologous bladder muscle cell-alginate suspension ($40$–$60 \times 10^6$ bladder muscle cells) were injected through the needle, while lifting of the ureteral orifice was endoscopically visualized. The left ureteral orifice remained untreated and served as a control. Serial cystograms, cystoscopy, and excretory urographic studies were performed at eight week intervals until sacrifice. The mini-pigs were sacrificed at eight (1), 16 (1), and 26 (2) weeks after treatment. The bladder injection sites were resected and examined macroscopically and microscopically. Specimens were stained with hematoxylin and eosin, and alcian blue at a pH of 1.0 and 2.5. Histological analyses of the bladder, ureters, regional lymph nodes, kidneys, liver, and spleen were performed.

Results

Four mini-swine underwent bilateral creation of reflux. All four were found to have bilateral reflux without evidence of obstruction at three months following the procedure. Bladder muscle cells were from each mini-swine and expanded in vitro. The animals then underwent endoscopic repair of reflux with the injectable autologous bladder muscle cell-alginate gel solution on the right side only.

Cystoscopic and radiographic examinations were performed at two, four, and six months after treatment. Cystoscopic examinations showed a smooth bladder wall. Cystograms showed no evidence of reflux on the treated side and persistent reflux in the uncorrected control ureter in all animals. All animals had a successful cure of reflux in the repaired ureter without evidence of hydronephrosis on excretory urography.

At the time of sacrifice, gross examination of the bladder injection site showed the presence of bladder muscle cell-alginate composites in the subureteral region. Microscopic analyses of the tissues surrounding the injection site showed no inflammation. Tissue sections from the bladder, ureters, lymph nodes, kidneys, liver and spleen showed no evidence of alginate migration or granuloma formation.

SUMMARY OF EXPERIMENTAL DATA

Autologous bladder muscle cells can be readily harvested, expanded in vitro, and injected cystoscopically. The cells survive and form a muscle nidus which is non-antigenic. This system is able to correct reflux without any evidence of obstruction.

Modifications and variations of the present invention will be obvious to those skilled in the art from the foregoing detailed description. Such modifications and variations are intended to come within the scope of the appended claims.

We claim:

1. A method for treating conditions which require the reconstruction of an anatomical area selected from the group consisting of the thoracic region, gastrointestinal tract, urinary tract, and reproductive tract comprising injecting into a patient in need of treatment thereof at a site in the anatomical area a suspension of smooth muscle cells in a biodegradable non-proteinaceous polymer solution that forms an ionically crosslinked hydrogel having the cells dispersed therein when injected in vivo, which becomes a non-migratory, volume stable tissue mass.

2. The method of claim 1 wherein the polymer is crosslinkable by temperature or pH and is selected from the group consisting of polysaccharides, polyphosphazines, polyacrylates, and polyethylene oxide-polypropylene glycol block copolymers.

3. The method of claim 2 wherein the polymers have acidic side groups that can be reacted with cations and are selected from the group of polymers consisting of poly (phosphazenes), poly(acrylic acids), poly(methacrylic acids), copolymers of acrylic acid and methacrylic acid, poly(vinyl acetate), sulfonated polymers, and copolymers having acidic side groups formed by reaction of acrylic or methacrylic acid and vinyl ether monomers or polymers.

4. The method of claim 2 wherein the polymers have basic side groups that can be reacted with anions and are selected from the group of polymers consisting of poly(vinyl amines), poly(vinyl pyridine), poly(vinyl imidazole), and imino substituted polyphosphazenes.

5. The method of claim 2 wherein the polymer is selected from the group consisting of alginate and hyaluronic acid.

6. The method of claim 1 wherein the muscle cells are isolated from the patient.

7. The method of claim 1 wherein the condition is vesicoureteral reflux.

8. The method of claim 1 wherein the condition is incontinence.

9. The method of claim 1 wherein the area which requires reconstruction is in the thoracic region.

10. The method of claim 1 wherein the area which requires reconstruction is in the upper gastrointestinal tract.

11. A method for obstructing a lumen or tube in a patient in need of treatment thereof comprising injecting into the lumen or tube in the patient a suspension of autologous muscle cells in a biodegradable polymer solution that forms a hydrogel having the cells dispersed therein which becomes a non-migratory, volume stable tissue mass.

12. The method of claim 11 wherein the polymer can be crosslinked by a change in pH, addition of multivalent ion, or a change in temperature.

13. The method of claim 11 wherein the polymer is a synthetic polymer.

14. The method of claim 13 wherein the polymers are selected from the group consisting of poly(phosphazenes) that can be crosslinked by reaction with cations, poly(acrylic acids), poly(methacrylic acids), copolymers of acrylic acid and methacrylic acid, poly(vinyl acetate), sulfonated polymers, copolymers having acidic side groups formed by reaction of acrylic or methacrylic acid and vinyl ether monomers or polymers, poly(vinyl amines), poly(vinyl pyridine), poly(vinyl imidazole), and imino substituted polyphosphazenes.

15. The method of claim 11 wherein the polymer is selected from the group consisting of fibrin, collagen, alginate, and hyaluronic acid.

16. The method of claim 11 wherein the tube is a fallopian tube.

17. The method of claim 1 wherein the area which requires reconstruction is a region adjacent to or a part of the rectum.

18. The method of claim 1 wherein the area which requires reconstruction is a region adjacent to or a part of the esophogus.

19. The method of claim 1 wherein the area which requires reconstruction is adjacent to or a part of the ureter.

* * * * *